US010894194B2

(12) United States Patent
Benson et al.

(10) Patent No.: US 10,894,194 B2
(45) Date of Patent: Jan. 19, 2021

(54) EAR-WEARABLE DEVICE PROVIDING GOLF ADVICE DATA

(71) Applicant: Starkey Laboratories, Inc., Eden Prairie, MN (US)

(72) Inventors: Craig Benson, Hopkins, MN (US); Christopher L. Howes, Eden Prairie, MN (US); David Tourtelotte, Eden Prairie, MN (US); Sidney A. Higgins, Maple Grove, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 85 days.

(21) Appl. No.: 15/690,001

(22) Filed: Aug. 29, 2017

(65) Prior Publication Data
US 2019/0060733 A1   Feb. 28, 2019

(51) Int. Cl.
*A63B 69/36* (2006.01)
*H04W 4/02* (2018.01)
(Continued)

(52) U.S. Cl.
CPC .......... *A63B 69/36* (2013.01); *A63B 24/0003* (2013.01); *A63B 24/0062* (2013.01); *A63B 71/0622* (2013.01); *A63B 71/0669* (2013.01); *G09B 5/04* (2013.01); *G16H 20/30* (2018.01); *G16H 40/63* (2018.01); *H04B 1/086* (2013.01); *H04W 4/02* (2013.01); *H04W 4/027* (2013.01); *A63B 2071/063* (2013.01); *A63B 2071/0655* (2013.01); *A63B 2220/12* (2013.01); *A63B 2220/17* (2013.01); *A63B 2220/20* (2013.01);
(Continued)

(58) Field of Classification Search
CPC .......... H04R 1/01; H04R 25/554; A63B 69/36
See application file for complete search history.

(56) References Cited

U.S. PATENT DOCUMENTS 7,733,224 B2   6/2010   Tran
7,929,713 B2   4/2011   Victorian et al.
(Continued)

FOREIGN PATENT DOCUMENTS

EP         2033488 B1      3/2013
WO      2008151623 A1    12/2008
(Continued)

OTHER PUBLICATIONS

International Search Report and Written Opinion of International Application No. PCT/US2018/048297, dated Oct. 29, 2018, 15 pp.
(Continued)

*Primary Examiner* — Tramar Y Harper
*Assistant Examiner* — Jeffrey K Wong
(74) *Attorney, Agent, or Firm* — Shumaker & Sieffert, P.A.

(57) ABSTRACT

A computing system wirelessly receives data from an ear-wearable device and determines, based on the data received from the ear-wearable device, a current position of the ear-wearable device. Additionally, the computing system determines, based on the current position of the ear-wearable device and data regarding a golf course, golf advice data that provides a recommendation regarding play of the golf course. Furthermore, the computing system wirelessly sends audio data to the ear-wearable device. The audio data represents soundwaves of a vocalization of the golf advice data.

30 Claims, 8 Drawing Sheets

(51) Int. Cl.
*H04B 1/08* (2006.01)
*A63B 71/06* (2006.01)
*A63B 24/00* (2006.01)
*G09B 5/04* (2006.01)
*G16H 20/30* (2018.01)
*G16H 40/63* (2018.01)

(52) U.S. Cl.
CPC ....... *A63B 2220/40* (2013.01); *A63B 2220/76* (2013.01); *A63B 2220/806* (2013.01); *A63B 2220/808* (2013.01); *A63B 2220/836* (2013.01); *A63B 2225/50* (2013.01); *A63B 2230/06* (2013.01); *A63B 2230/50* (2013.01)

(56) References Cited

U.S. PATENT DOCUMENTS

| | | | |
|---|---|---|---|
| 8,374,367 | B2 | 2/2013 | Nielsen et al. |
| 2008/0085778 | A1* | 4/2008 | Dugan ............... A63B 69/3623 473/223 |
| 2008/0235026 | A1 | 9/2008 | Garratt et al. |
| 2008/0254916 | A1* | 10/2008 | Kim ....................... A63B 71/06 473/407 |
| 2011/0137141 | A1 | 6/2011 | Razoumov et al. |
| 2016/0353496 | A1* | 12/2016 | Egendorf ............... G06Q 30/02 |
| 2017/0311092 | A1* | 10/2017 | Secall ................... H04R 25/554 |
| 2017/0333755 | A1* | 11/2017 | Rider ...................... A63B 21/06 |
| 2017/0347183 | A1* | 11/2017 | Masaki ................. H04R 1/1016 |
| 2018/0137359 | A1* | 5/2018 | Dayal ................. G06K 9/00684 |

FOREIGN PATENT DOCUMENTS

| | | |
|---|---|---|
| WO | 2008151624 A1 | 12/2008 |
| WO | 2008151638 A1 | 12/2008 |
| WO | 2010149157 A1 | 12/2010 |
| WO | 2011038767 A1 | 4/2011 |

OTHER PUBLICATIONS

International Preliminary Report on Patentability from International Application No. PCT/US2018/048297, dated Mar. 12, 2020, 10 pp.

* cited by examiner

EAR-WEARABLE DEVICE PROVIDING GOLF ADVICE DATA

TECHNICAL FIELD

This disclosure relates to ear-wearable devices.

BACKGROUND

Golf is a game enjoyed by millions of people around the world. Each shot in the game of golf requires the golfer to make numerous decisions. For instance, the golfer must choose which club to use, how hard to hit the ball, what angles to use to avoid hazards, and so on. To make these decisions effectively, golfers want accurate information and advice. Accordingly, smartphone-based golf assistance applications have been developed that attempt to provide various types of information to golfers. However, as described in this disclosure, there are several shortcomings associated with such smartphone-based golf assistance applications.

SUMMARY

This disclosure describes techniques related to use of ear-wearable devices in assisting golfers. For example, one technique improves location accuracy for purposes of providing golf advice data. As described herein, a computing system may wirelessly receive data from an ear-wearable device. Furthermore, the computing system may determine, based on the data received from the ear-wearable device, a current position of the ear-wearable device. The computing system may also determine, based on the current position of the ear-wearable device and data regarding a golf course, golf advice data that provides a recommendation regarding play of the golf course. Furthermore, the computing system may wirelessly send audio data to the ear-wearable device, the audio data representing soundwaves of a vocalization of the golf advice data.

In one example, this disclosure describes a method comprising: wirelessly receiving, by a computing system, data from an ear-wearable device, the computing system comprising one or more electronic computing devices; determining, by the computing system, based on the data received from the ear-wearable device, a current position of the ear-wearable device; determining, by the computing system, based on the current position of the ear-wearable device and data regarding a golf course, golf advice data that provides a recommendation regarding play of the golf course; and wirelessly sending, by the computing system, audio data to the ear-wearable device, the audio data representing soundwaves of a vocalization of the golf advice data.

In another example, this disclosure describes a computing system comprising: a radio; and one or more electronic computing devices configured to: configure the radio to wirelessly receive data from an ear-wearable device; determine, based on the data received from the ear-wearable device, a current position of the ear-wearable device; determine, based on the current position of the ear-wearable device and data regarding a golf course, golf advice data that provides a recommendation regarding play of the golf course; and cause the radio to wirelessly send audio data to the ear-wearable device, the audio data representing soundwaves of a vocalization of the golf advice data.

In another example, this disclosure describes a non-transitory computer-readable storage medium having instructions stored thereon that, when executed, cause a computing system comprising one or more electronic computing devices to: configure a radio of the computing system to wirelessly receive data from an ear-wearable device; determine, based on the data received from the ear-wearable device, a current position of the ear-wearable device; determine, based on the current position of the ear-wearable device and data regarding a golf course, golf advice data that provides a recommendation regarding play of the golf course; and cause the radio to wirelessly send audio data to the ear-wearable device, the audio data representing soundwaves of a vocalization of the golf advice data.

In another example, this disclosure describes a method comprising: generating, by an ear-wearable device, based on signals from one or more sensors integrated into the ear-wearable device, movement data representing movement of the ear-wearable device; wirelessly sending, by the ear-wearable device, the movement data to a computing system; wirelessly receiving, by the ear-wearable device, audio data representing a vocalization of golf advice data based on a current position of the ear-wearable device on a golf course, wherein the golf advice data is determined in part based on the movement data; and outputting, by the ear-wearable device, sound of the vocalization of the golf advice data.

In another example, this disclosure describes an ear-wearable device comprising: a radio; one or more sensors; a receiver; and one or more processors configured to: generate, based on signals from the one or more sensors, movement data representing movement of the ear-wearable device; cause the radio to wirelessly send the movement data to a computing system; configure the radio to wirelessly receive audio data representing a vocalization of golf advice data based on a current position of the ear-wearable device on a golf course, wherein the golf advice data is determined in part based on the movement data; and cause the receiver to output sound of the vocalization of the golf advice data.

In another example, this disclosure describes a method comprising: wirelessly receiving, by a computing system, from a laser range finder, data indicating a distance from the laser range finder to a target location; and wirelessly sending, by the computing system, audio data to an ear-wearable device, the audio data representing soundwaves of a vocalization of the distance.

In another example, this disclosure describes a laser range finder comprising: a radio; a laser configured to emit a laser beam; a laser detector configured to detect a reflection of the laser beam; circuitry configured to: determine, based on the reflection of the laser beam, a distance to a target location; cause the radio to wirelessly send, to a remote device, data indicating the distance.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
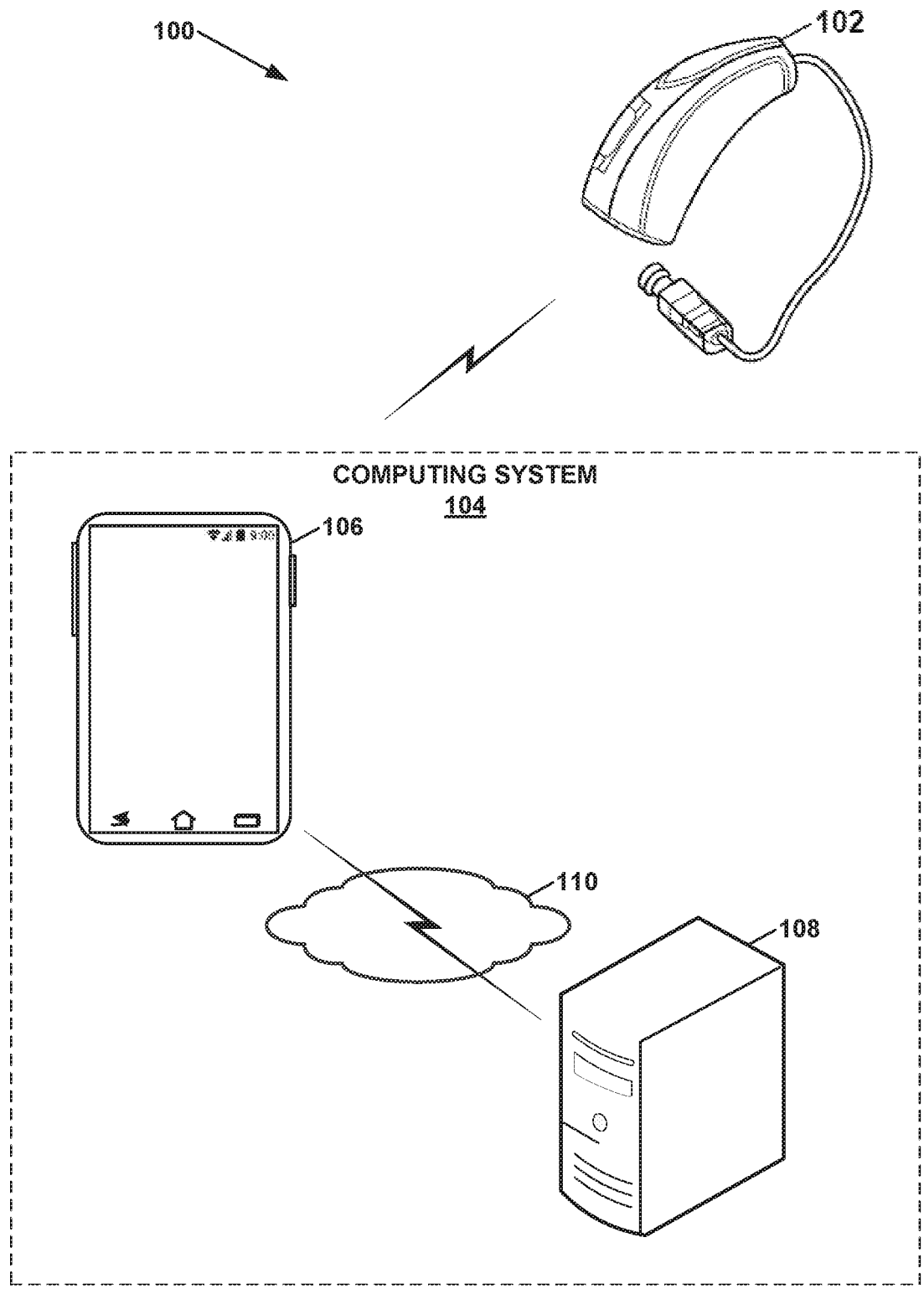
FIG. 1 illustrates an example system for providing golf advice data to a wearer of an ear-wearable device, in accordance with one or more aspects of this disclosure.

In this disclosure, ordinal terms such as "first," "second," "third," and so on, are not necessarily indicators of positions within an order, but rather may simply be used to distinguish different instances of the same thing. Examples provided in this disclosure may be used together, separately, or in various combinations.

In general, this disclosure describes techniques for providing golf advice data to a wearer of an ear-wearable device. A golfer may find certain types of information extremely helpful when playing golf. For example, a golfer may want to know how far it is from the golfer's current location to the pin on a hole of a given golf course. In another example, a golfer may want to know what club would be the best choice given the golfer's current location. Other types of information that a golfer may want to know may include a speed of a green, the existence of hazards in the golf course, the wind speed, a target position at which to aim a next shot (e.g., preferred landing zones), an elevation change between a current position of the golfer and the target position at which to aim the next shot, and so on. This disclosure may refer to information that provides a recommendation regarding golf as golf advice data.

In the past, applications (i.e., golf assistance applications) have been developed for mobile devices, such as smartphones, that attempt to provide golfers with certain types of golf advice data. Such golf assistance applications may use location information from the location-determination resources of the mobile devices on which the golf assistance applications run. For instance, a golf assistance application running on a mobile device may use location information from a Global Navigation Satellite System (GLASS) resource of the mobile device. Example types of GNSS's include the Global Positioning System (GPS), the European Galileo system, the Russian GLONASS system, the Chinese BeiDou system, and so on.

As described herein, techniques of this disclosure may overcome technical challenges associated with devices that run golf assistance applications. For example, golfers frequently leave their mobile devices in their golf carts because golfers often find it uncomfortable to carry their mobile devices in their pockets during play as many golfers find that wearing or carrying a mobile device interferes with their swings. However, golfers that leave their mobile devices behind in their golf carts may move considerable distances from their golf carts prior to actually hitting shots. This is especially true in cases (e.g., during wet conditions) where golf courses disallow users from driving golf carts off paved tracks. As a result, the position from which a golfer is actually playing may differ significantly from a location of the mobile device running a golf assistance application. Hence, in such situations, location-dependent golf information provided by devices running such golf assistance applications may have significant inaccuracies.

In accordance with particular techniques of this disclosure, a radio of a computing system wirelessly receives data from an ear-wearable device. For example, the ear-wearable device comprises a hearing aid device. The computing system comprises one or more electronic computing devices, such as smartphone. In this example, the computing system determines, based on the data received from the ear-wearable device, a current position of the ear-wearable device. Additionally, the computing system may determine, based on the current position of the ear-wearable device and data regarding a golf course, golf advice data that provides a recommendation regarding play of the golf course. In this example, the radio of the computing system may wirelessly send audio data to the ear-wearable device. The audio data may represent soundwaves of a vocalization, such as human speech or audible tones, of the golf advice data. In this example, by using data from the ear-wearable device, the computing system may establish a more accurate location of the golfer. As an additional advantage, sending the audio data to the ear-wearable device may spare the golfer from the inconvenience of needing to go back to a golf cart or other location to view the golf advice data.

FIG. 1 illustrates an example system 100 for providing golf advice data to a wearer of an ear-wearable device 102, in accordance with one or more aspects of this disclosure. As shown in the example of FIG. 1, system 100 includes an ear-wearable device 102 and a computing system 104. Computing system 104 comprises one or more electronic computing devices. For instance, in the example of FIG. 1, computing system 104 comprises a mobile device 106, a server device 108, and a communication network 110. In other examples, computing system 104 may be implemented in different ways. For instance, mobile device 106 may perform some or all of the functions described in this disclosure as being performed by server device 108. Thus, in some such examples, computing system 104 does not include server device 108 or communication network 110. Moreover, in some examples, server device 108 may perform particular actions described in this disclosure as being performed by mobile device 106. Thus, in general, descriptions in this disclosure of computing system 104 performing particular actions may be interpreted as mobile device 106, server device 108, or some combination of mobile device 106 and server device 108 and/or another device, performing the particular actions.

Ear-wearable device 102 may comprise various types of devices designed to be worn in and/or on an ear of a wearer. For example, ear-wearable device 102 may comprise a hearing aid device, a wireless headset, a wireless earbud, or another type of device. The type of ear-wearable device shown in FIG. 1 is merely one example type of ear-wearable devices that may be used with techniques of this disclosure.

Mobile device 106 may comprise various types of computing devices designed for mobility. For example, mobile device 106 may comprise a smartphone, a tablet computer, a portable media player device, a Global Navigation Satellite System (GNSS) device, or another type of device designed for mobile use.

Mobile device 106 may communicate with server device 108 via communication network 110. Communication network 110 may comprise a cellular communication network, such as a 4G LTE network, a 5G network, or a cellular communication network using another type of wireless communication technology. Communication network 110 may comprise or be coupled to the Internet. Server device 108 may comprise various types of computing devices. For example, server device 108 may comprise a standalone server device, a server blade, a personal computer, a content delivery network device, or another type of device.

Ear-wearable device 102 is communicatively coupled to mobile device 106. That is, two-way communication may occur between ear-wearable device 102 and mobile device 106. Ear-wearable device 102 and mobile device 106 may communicate using various wireless communication technologies. For example, ear-wearable device and mobile device 106 may communicate using Bluetooth, WiFi, Zigbee, or another wireless communication technology.

Computing system 104 may access data regarding a golf course. For instance, in some examples, server device 108 stores data regarding the golf course and mobile device 106 retrieves the data regarding the golf course from server device 108. In some examples, server device 108 stores data regarding the golf course and mobile device 106 provides information, such as position information, to server device 108, that enables server device 108 to access data regarding the golf course.

Computing system 104 may access, from local storage or a network resource such as a remote server, various types of data regarding a golf course. For example, the data regarding the golf course may include map data for holes of the golf course. Such map data may include information identifying locations of water hazards, sand traps, fairways, greens, roughs, cart paths, refreshment stations, trees, obstacles, pins, cups, tee boxes, out-of-bounds markers to identify regions that are out of bounds, waste bunkers, light rough, intermediate rough, long rough, flower gardens and other keep-out areas, course maintenance areas, and other features associated with positions in a golf course. In some examples, the data regarding the golf course may include weather data for the golf course, such as wind speed and direction, par information for holes of the golf course, and other types of information. Furthermore, in some examples, the data regarding the golf course may include data regarding a person's past play of the golf course, such as the person's previous scores and club selections for individual holes of the golf course.

In accordance with one or more techniques of this disclosure, computing system 104 may wirelessly receive data from ear-wearable device 102. Additionally, computing system 104 may determine, based on the data received from ear-wearable device 104, a current position of ear-wearable device 102. Computing system 104 may determine, based on the current position of ear-wearable device 102 and data regarding a golf course, golf advice data that provides a recommendation regarding play of the golf course. Furthermore, computing system 104 may wirelessly send audio data to ear-wearable device 102. The audio data may represent soundwaves of a vocalization of the golf advice data.

In various examples, computing system 104 determines the current position of ear-wearable device 102 in different ways. For instance, in one example, computing system 104 determines, based on Global Navigation Satellite System (GNSS) data, an initial location of the ear-wearable device at a time when a signal strength of a radio signal generated by ear-wearable device 102 as detected by the radio of computing system 104 is above a threshold. For instance, if the signal strength of the radio signal generated by ear-wearable device 102 is above the threshold, computing system 104 may determine that ear-wearable device 102 is sufficiently close to mobile device 106 to assume that the current location of ear-wearable device 102 is substantially the same as the current location of mobile device 106. In this example, the data received from ear-wearable device 102 comprises data indicative of movements of ear-wearable device 102. For instance, the data received from ear-wearable device 102 may comprise accelerometer data generated by accelerometers integrated into ear-wearable device 102. In some examples, the data received from ear-wearable device 102 may comprise orientation data generated by one or more gyroscopes and/or magnetic field detectors (e.g., compasses) integrated into ear-wearable device 102. Furthermore, in this example, computing system 104 may determine the current position of ear-wearable device 102 by calculating, via dead reckoning using the initial location of ear-wearable device 102 and the data indicative of the movements of ear-wearable device 102, the current position of ear-wearable device 102. In other words, computing system 104 may use the data indicative of the movement of ear-wearable device 102 to determine the displacement of ear-wearable device 102 relative to the initial location of ear-wearable device 102. For instance, in examples where the data indicative of the movements of ear-wearable device 102 comprises accelerometer data and directionality data, computing system 104 may determine that ear-wearable device 102 moved 1.5 meters north, 6 meters west, and so on. The directionality data may comprise data from a compass and/or a gyroscope included in ear-wearable device 102. In some examples, ear-wearable device 102 receives initial location information from computing system 104 and ear-wearable device 102 itself determines, via dead reckoning using data indicative of movements of ear-wearable device 102, the current position of ear-wearable device 102. In this example, ear-wearable device 102 may send data indicating the current position of ear-wearable device 102 to computing system 104.

In other examples, computing system 104 determines the current position of ear-wearable device 102 based on GNSS data included in the data received from ear-wearable device 102. That is, in some examples, ear-wearable device 102 itself includes a GNSS unit that determines a position of ear-wearable device 102 and sends GNSS data indicating the determined position to computing system 104, e.g., via mobile device 106.

Computing system 104 may determine various types of golf advice data based on where the current position of ear-wearable device 102 is on a golf course. For example, the golf advice data may include a recommendation of a golf club, a distance of ear-wearable device 102 to a pin, a distance of ear-wearable device 102 to the center, back, or front of a green, a distance of ear-wearable device 102 to a front, center, or back of a hazard, a target position on the golf course at which to aim a next shot, an elevation change between the current position of the ear-wearable device and the target position on the golf course of the next shot, wind conditions at the current position of the ear-wearable device, existence of hazards in the golf course, reminders about balls breaking toward water, or a speed of a green (e.g., as determined using regularly-refreshed stimpmeter data). Other types of golf advice data may include timing information related to a conclusion/start of a tournament on the course, warnings of dangerous animals (alligators, snakes, bears) at specific course locations, notifications regarding events, such as dangerous people invading a golf course, indications regarding where golfers should seek shelter, weather alerts, and so on.

As mentioned above, the golf advice data may include a recommendation of a golf club. Computing system 104 may determine the recommended golf club in various ways. For example, computing system 104 may determine, based on the current position of ear-wearable device 102, whether ear-wearable device 102 is in a sand trap. If so, computing system 104 may recommend a sand wedge. Otherwise, if ear-wearable device 102 is not in a sand trap, computing system 104 may determine a distance (and, in some examples, other factors) from a current position of ear-wearable device 102 to a pin or to a target location of the wearer's next shot. Computing system 104 may then use the determined distance (and, in some examples, other factors) to look up, in a lookup table or other data structure, a suggested club. The other factors may include elevation change, wind speed, wind direction, a history of previously used clubs, and so on.

Ear-wearable device 102 comprises a microphone that detects incoming soundwaves. For example, the microphone may detect the sound of the voice of the wearer of ear-wearable device 102. In some examples, ear-wearable device 102 generates and wirelessly transmits audio data representing the incoming soundwaves. Ear-wearable device 102 may generate the audio data according to any of a variety of audio encoding or vocoding technologies known in the art. Computing system 104 may wirelessly receive the audio data from ear-wearable device 102. Computing system 104 may use the audio data for various purposes. For example, computing system 104 may determine, based on the audio data and based on data regarding the golf course, golf advice data that provides a recommendation regarding play of the golf course. In this example, a radio of computing system 104 may wirelessly send audio data to ear-wearable device 102 that represents soundwaves of a vocalization of the determined golf advice data.

This behavior may enable a wearer of ear-wearable device 102 to vocally request the golf advice data without needing to physically access mobile device 106. For example, the incoming soundwaves detected by ear-wearable device 102 may represent a question regarding the golf course (e.g., distance to pin, club recommendation, etc.) or environmental conditions (e.g., wind speed, wind direction, temperature, etc.) at the golf course. In this example, computing system 104 may determine, based on the audio data and based on the data regarding the golf course, the golf advice data such that the golf advice data comprises an answer to the question. For example, the wearer of ear-wearable device 102 may ask out loud how far away is the pin of a hole that the wearer is currently playing. In this example, computing system 104 may send back audio data representing a vocalization of the answer to this question (e.g., 75 yards). Computing system 104 may use various speech recognition techniques known in the art for interpreting the audio data and synthesizing the vocalization of the answer.

In some examples, ear-wearable device 102 sends a request to mobile device 106 in response to receiving physical input from a user. For example, ear-wearable device 102 may comprise a button. In this example, ear-wearable device 102 sends a request for golf advice data to mobile device 106 in response to detecting that the button has been depressed. In some examples, ear-wearable device 102 comprises one or more accelerometers. In this example, ear-wearable device 102 sends a request for golf advice data to mobile device 106 in response to detecting signals from the one or more accelerometers consistent with a user tapping ear-wearable device 102. In such examples, computing system 104 may respond to the request with audio data representing a vocalization of a predetermined type of golf advice data.

In some examples, computing system 104 may use data received from ear-wearable device 102 to help a wearer of ear-wearable device 102 improve the wearer's golf swing. For example, computing system 104 may wirelessly receive from ear-wearable device 102 data indicative of movements of ear-wearable device 102. The data indicative of the movements of ear-wearable device 102 may be generated based on signals from multi-axis accelerometers. In this example, computing system 104 may determine, based on the data indicative of the movements of ear-wearable device 102, golf advice data that provides a recommendation on improving a golf swing. In this example, a radio of computing system 104 may wirelessly send audio data to ear-wearable device 102. The audio data sent to ear-wearable device 102 may represent soundwaves of a vocalization of this golf advice data. For example, computing system 104 may interpret the data indicative of movements of ear-wearable device 102 as indicating that the wearer of ear-wearable device 102 has lifted the wearer's head during a swing, or swaying during the swing, which are well-known technique problems. Alignment, posture and set-up errors may also be detected. Many of these errors may not be detected using sensors in a smartphone carried in a user's pocket. In some examples, computing system 104 may interpret the data indicative of movements of ear-wearable device 102 as indicating a hitch, pause, under-rotation, or over-rotation in the wearer's backswing.

In some examples, computing system 104 may use data from accelerometers in ear-wearable device 102 and data from specialized golf swing analysis hardware to analyze a golfer's swing. For example, computing system 104 may determine that the golfer is using an outside-in swing plane, swinging at too fast of a tempo, prematurely turning their head or lifting their head, or other faults. This feedback can be useful for a golfer who begins to struggle with the long game, and could help immediately correct their swing faults, and improve their play. In some examples, the accelerometers in ear-wearable device 102 serve as a practice metronome, to monitor and gauge swing tempo, which happens to be another common fault. In some examples, the sound of the ball being struck at impact determines when the actual golf swing is made, differentiating it from practice swings.

Computing system 104 may use the data regarding the current position of ear-wearable device 102 for various purposes in addition to providing golf advice data. For example, computing system 104 may use the data regarding the current position of ear-wearable device 102 to determine that the wearer of ear-wearable device 102 has completed a hole of the golf course and to request the wearer provide a score or other information for the hole. For instance, in this example, computing system 104 may determine, based on the current position of ear-wearable device 102 that a wearer of ear-wearable device 102 has completed play of a hole of the golf course. In this example, in response to determining that the wearer of ear-wearable device 102 has completed play of the hole, computing system 104 may wirelessly send audio data to ear-wearable device 102. In this example, the audio data may represent soundwaves of a vocalization of a prompt to the wearer of ear-wearable device 102 to provide play result information for the hole. Furthermore, in this example, a radio of computing system 104 may wirelessly receive audio data from ear-wearable device 102. In this example, the audio data may represent soundwaves of a vocalization of the play result information. In this example, responsive to wirelessly receiving the audio data, computing system 104 may store the play result information for subsequent retrieval. In this example, the play result information may include one or more of a score for the hole, a number of putts, a number of fairway hits and misses, a number of sand shots, a number of penalty shots, a distance a ball was hit by a golf club, or other information describing results of playing the hole.

Computing system 104 may determine that the wearer of ear-wearable device 102 has completed play of a hole in various ways. For example, computing system 104 may determine that ear-wearable device 102 was within a particular distance of a pin of the hole and then moved to a tee box of another hole of the golf course or a sufficient distance from the pin of the hole.

In addition to providing the types of golf information described above, computing system 104 may determine a pace of play of the wearer of ear-wearable device 102. Computing system 104 may determine whether the wearer's pace of play is too slow or too fast based on the current position of ear-wearable device 102, data regarding expected times for completing holes of the golf course, data provided about the pace of other players on the golf course (possibly by the golf course or by other golfers using the same or comparable applications), and data regarding a starting time of the wearer's play of the golf course, and so on. Computing system 104 may wirelessly send audio data to ear-wearable device 102 representing a vocalization indicating whether the wearer should speed up play, or whether the wearer can slow down play if desired.

In some examples, ear-wearable device 102 comprises one or more sensors that collect biometric data regarding a wearer of ear-wearable device 102. For example, ear-wearable device 102 may comprise a body temperature sensor that measures the body temperature of the wearer, one or more sensors for determining a heart rate of the wearer, a galvanic skin response (GSR) sensor, number of steps taken, and so on. Ear-wearable device 102 may wirelessly transmit the biometric data to computing system 104. Computing system 104 may use the biometric data for various purposes. For example, computing system 104 may use the biometric data to determine whether it is safe for the wearer of ear-wearable device 102 to continue playing golf and to notify the wearer if it is not safe to continue play. Thus, in this example, a radio of computing system 104 may wirelessly receive biometric data from ear-wearable device 102. In this example, the biometric data may comprise at least one of heartrate information, body temperature information, number of steps taken, or GSR information. Furthermore, in this example, computing system 104 may determine, based on the biometric data, whether a wearer of ear-wearable device 102 should stop play of the golf course. Responsive to determining the wearer of ear-wearable device 102 should stop play of the golf course, computing system 104 may wirelessly send audio data to ear-wearable device 102. The audio data may represent soundwaves of a vocalization of advice to stop play of the golf course. In some examples, computing system 104 may determine that the wearer should stop play of the golf course if the wearer's heart rate and/or body temperature rise above particular thresholds, and/or if the wearer has taken more than a particular number of steps in a given time period. In some examples, computing system 104 stores records of the biometric data for future reference.

Figure 2:
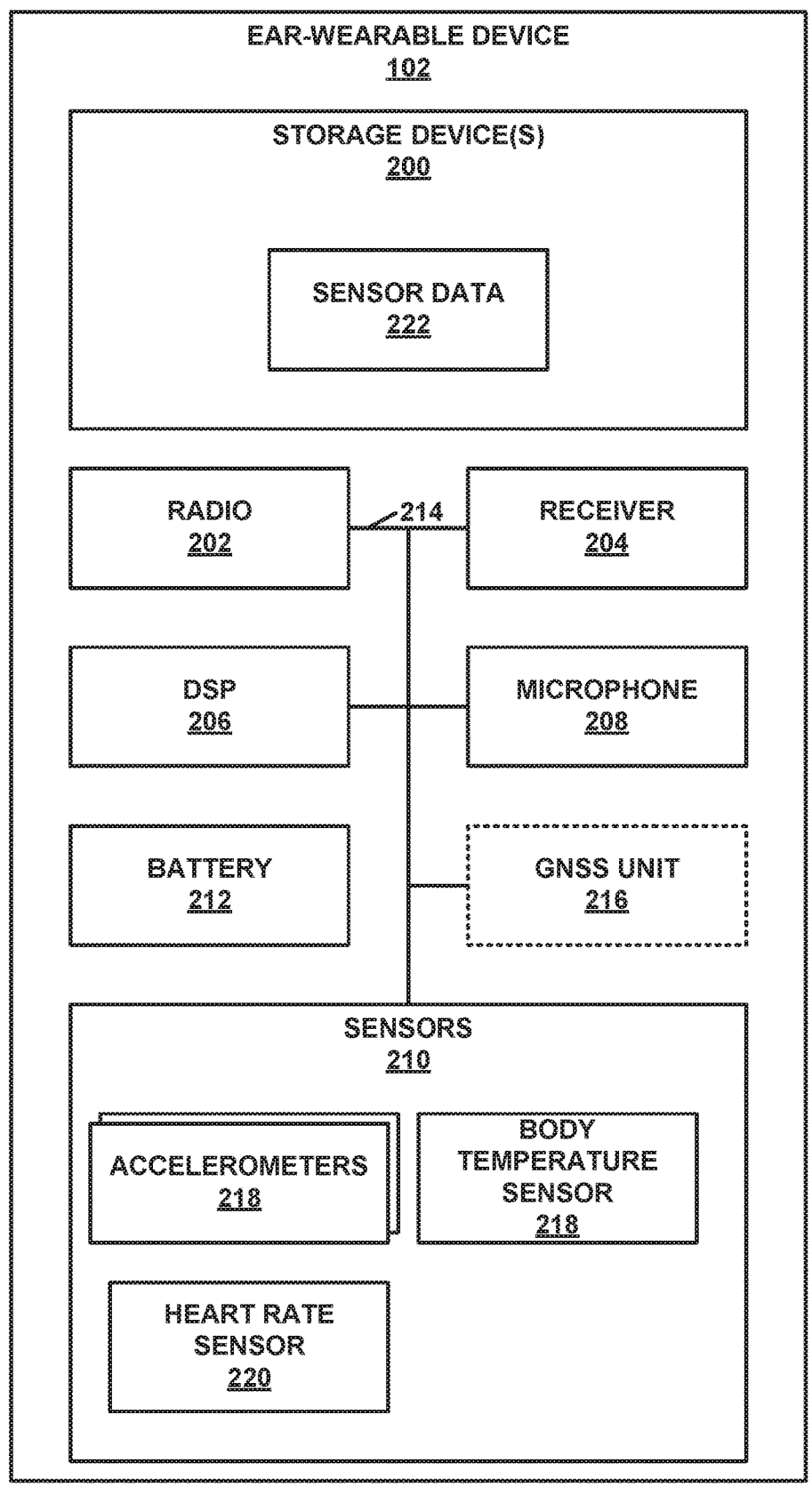
FIG. 2 is a block diagram illustrating example components of an ear-wearable device, in accordance with one or more aspects of this disclosure.

FIG. 2 is a block diagram illustrating example components of ear-wearable device 102, in accordance with one or more aspects of this disclosure. In the example of FIG. 2, ear-wearable device 102 comprises one or more storage device(s) 200, a radio 202, a receiver 204, a digital signal processor (DSP) 206, a microphone 208, a set of sensors 210, a battery 212, and one or more communication channels 214. Furthermore, in some examples, ear-wearable device 102 comprises a GNSS unit 216. Communication channels 212 provide communication between storage device(s) 200, radio 202, receiver 204, DSP 206, a microphone 208, sensors 210, and, if present, a GNSS unit 216. Components 200, 202, 204, 206, 208, 210, 214, and 216 draw electrical power from battery 212. In some examples, battery 212 is rechargeable.

In the example of FIG. 2, sensors 208 include one or more accelerometers 218. Additionally, in the example of FIG. 2, sensors 210 also include a body temperature sensor 218 and a heart rate sensor 220. In other examples, ear-wearable device 102 may include more, fewer, or different components. For instance, in other examples, ear-wearable device 102 does not include GNSS unit 216, or particular sensors shown in the example of FIG. 2. In some examples, heart rate sensor 220 comprises a visible light sensor and/or a pulse oximetry sensor. Storage device(s) 200 may store data. In some examples, storage device(s) 200 may comprise volatile or non-volatile memory.

Radio 202 may enable ear-wearable device 102 to send data to and receive data from one or more other computing devices. For example, radio 202 may enable ear-wearable device 102 to send data to and receive data from mobile device 106 (FIG. 1), Radio 202 may use various types of wireless technology to communicate. For instance, radio 202 may use Bluetooth, 3G, 4G, 4G LTE, ZigBee, WiFi, or another communication technology.

Receiver 204 comprises one or more speakers for generating audible sound. Microphone 208 detects incoming sound and generates an electrical signal (e.g., an analog or digital electrical signal) representing the incoming sound. In examples where ear-wearable device 102 acts as a hearing assistance device (e.g., a hearing aid device), DSP 206 may process the signal generated by microphone 208 to enhance, amplify, or cancel-out particular channels within the incoming sound. DSP 206 may then cause receiver 204 to generate sound based on the processed signal.

Sensors 210 may generate various types of signals. DSP 206 may use the signals generated by sensors 210 to generate sensor data. For example, DSP 206 may use signals generated by body temperature sensor 218 and heart rate sensor 220 to generate biometric data (e.g., data indicating a body temperature and heart rate of a wearer of ear-wearable device 102). In another example, DSP 206 may use signals from accelerometers 218 to generate movement data indicative of movements of ear-wearable device 102. In some examples, storage device(s) 200 may store sensor data 222 generated by DSP 206.

DSP 206 may cause radio 202 to transmit various types of data. For example, DSP 206 may cause radio 202 to transmit movement data, sensor data, or other types of data to computing system 104. Furthermore, in accordance with one or more techniques of this disclosure, DSP 206 may cause radio 202 to transmit audio data representing sound detected by microphone 208 to computing system 104 (FIG. 1). Furthermore, radio 202 may receive audio data from computing system 104 and DSP 206 may cause receiver 204 to output sound based on the audio data. In some examples where ear-wearable device 102 includes GNSS unit 216, DSP 206 may cause radio 202 to transmit GNSS data generated by GNSS unit 206.

Although sensors 210 are shown in the example of FIG. 2 as being part of ear-wearable device 102, one or more of sensors 210 may be included in other wearable devices that are communicatively linked with ear-wearable device 102. Examples of such wearable devices may include smartwatches, implantable medical devices, belt- or waist-worn devices, wearable fitness tracking devices, eye- or face-wearable devices, and other types of wearable devices.

In some examples, DSP 206 may use signals from accelerometers 218 to count the number of steps taken by a wearer of ear-wearable device 102. Ear-wearable device 102 may send this step count information to computing system 104 or another computing system. Thus, steps otherwise not counted by mobile device 106 (FIG. 1) because the wearer of ear-wearable device 102 has left mobile device 106 in a golf bag or cart may be counted. In this way, the wearer may obtain a more accurate step count.

In some examples, ear-wearable device 102 does not include electronics that provide audio amplification or may provide electronics to provide audio amplification to overcome insertion loss. In such examples, ear-wearable device 102 does not use algorithms or electronics to enhance speech intelligibility or provide frequency dependent amplification but could include such algorithms and electronics as a Personal Sound Amplification Product (PSAP)-style device with some adjustment capabilities. In some examples, ear-wearable device 102 is not programmable. In some examples, ear-wearable device 102 is a "plug-n-play" type of device. In some examples, ear-wearable device 102 is programmable to help the user manage things like wind noise. Furthermore, in some examples, ear-wearable device 102 comprises a custom earmold or a standard receiver module at the end of a RIC cable. The additional volume in a custom earmold may allow room for components such as sensors (accelerometers, heartrate monitors, temp sensors), a woofer-tweeter, (providing richer sound for music aficionados), and an acoustic valve that provides occlusion when desired. In some examples, a six-conductor RIC cable is used for in ear-wearable devices with sensors, woofer-tweeters, and/or acoustic valves.

Figure 3:
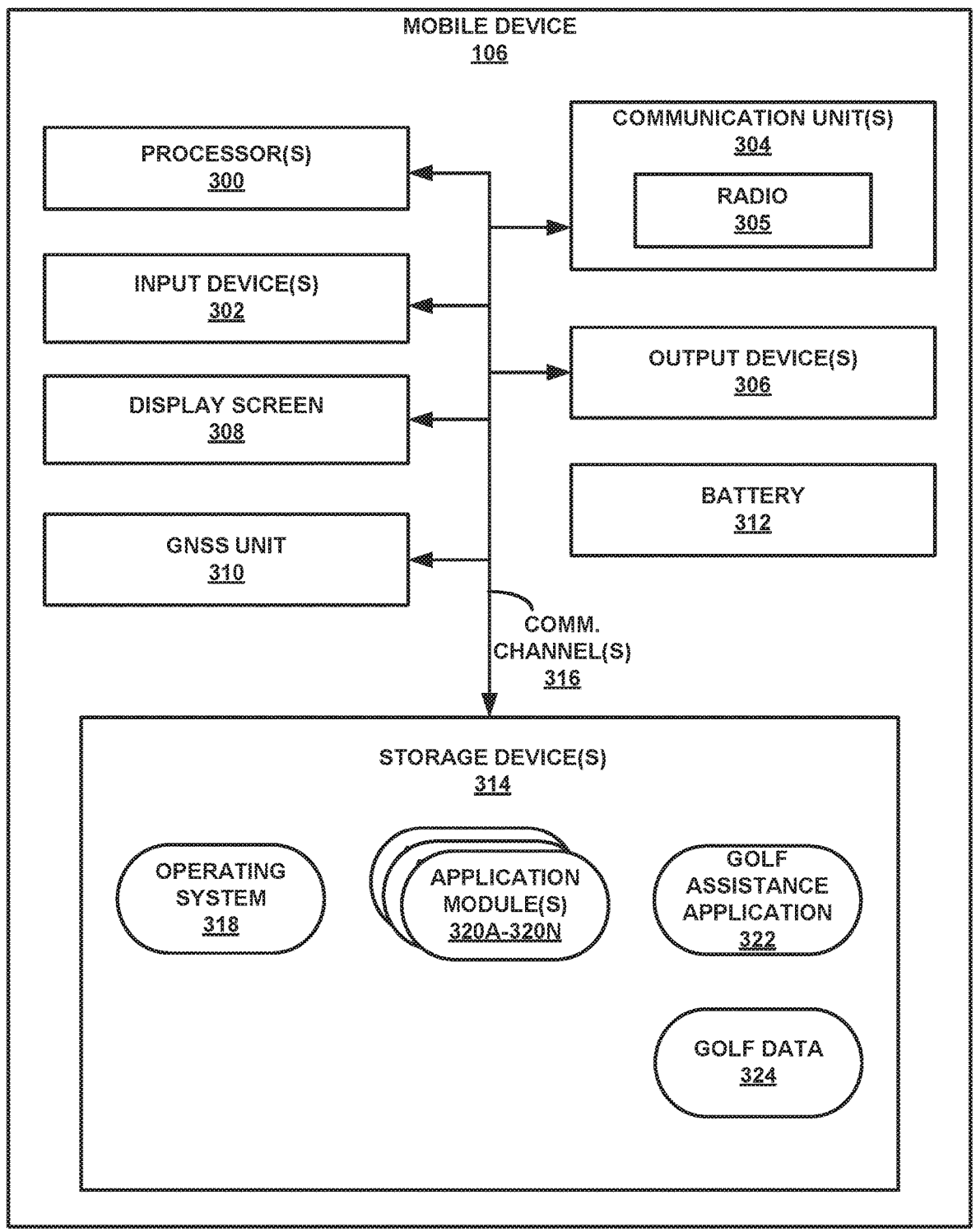
FIG. 3 is a block diagram illustrating example components of a mobile computing device, in accordance with one or more aspects of this disclosure.

FIG. 3 is a block diagram illustrating example components of mobile device 106, in accordance with one or more aspects of this disclosure. FIG. 3 illustrates only one particular example of mobile device 106, and many other example configurations of mobile device 106 exist.

As shown in the example of FIG. 3, mobile device 106 includes one or more processors 300, one or more input devices 302, one or more communication units 304, one or more output devices 306, a display screen 308, a GNSS unit 310, a battery 312, one or more storage devices 314, and one or more communication channels 316. Mobile device 106 may include many other components. For example, mobile device 106 may include physical buttons, microphones, speakers, communication ports, and so on. Communication channel(s) 316 may interconnect each of components 300, 302, 304, 306, 308, 310, and 314 for inter-component communications (physically, communicatively, and/or operatively). In some examples, communication channel(s) 316 may include a system bus, a network connection, an inter-process communication data structure, or any other method for communicating data. GNSS unit 310 may process GNSS signals to determine a current position of mobile device 106. Battery 312 may provide electrical energy to components 300, 302, 304, 306, 308, 310 and 314.

Storage device(s) 314 may store information required for use during operation of mobile device 106. In some examples, storage device(s) 314 have the primary purpose of being a short term and not a long-term computer-readable storage medium. Storage device(s) 314 may be volatile memory and may therefore not retain stored contents if powered off Storage device(s) 314 may further be configured for long-term storage of information as non-volatile memory space and retain information after power on/off cycles. In some examples, processor(s) 300 on mobile device 106 read and may execute instructions stored by storage device(s) 314.

Mobile device 106 may include one or more input device(s) 302 that mobile device 106 uses to receive user input. Examples of user input include tactile, audio, and video user input. Input device(s) 302 may include presence-sensitive screens, touch-sensitive screens, mice, keyboards, voice responsive systems, microphones or other types of devices for detecting input from a human or machine.

Communication unit(s) 304 may enable mobile device 106 to send data to and receive data from one or more other computing devices (e.g., via a communications network, such as a local area network or the Internet). In some examples, communication units) 304 may include wireless transmitters and receivers that enable mobile device 106 to communicate wirelessly with the other computing devices. For instance, in the example of FIG. 3, communication unit(s) 304 include a radio 305 that enables mobile device 106 to communicate wirelessly with other computing devices, such as ear-wearable device 102 (FIG. 1, FIG. 2). Examples of communication unit(s) 304 may include optical transceivers, radio frequency transceivers, or other types of devices that are able to send and receive information. Other examples of such communication units may include Bluetooth, 3G, and WiFi radios, Universal Serial Bus (USB) interfaces, etc. Mobile device 106 may use communication unit(s) 304 to communicate with one or more ear-wearable devices (e.g., ear-wearable device 102 (FIG. 1, FIG. 2)). Additionally, mobile device 106 may use communication unit(s) 304 to communicate with one or more other remote devices (e.g., server device 108 (FIG. 1)).

Output device(s) 306 may generate output. Examples of output include tactile, audio, and video output. Output device(s) 306 may include presence-sensitive screens, sound cards, video graphics adapter cards, speakers, liquid crystal displays (LCD), or other types of devices for generating output. In examples were one of output device(s) 306 includes a presence-sensitive screens, the output device may also be considered one of input devices 302.

Processor(s) 300 may read instructions from storage device(s) 314 and may execute instructions stored by storage device(s) 314. Execution of the instructions by processor(s) 300 may configure or cause mobile device 106 to provide at least some of the functionality ascribed in this disclosure to mobile device 106. As shown in the example of FIG. 3, storage device(s) 314 include computer-readable instructions associated with operating system 318, application modules 320A-320N (collectively, "application modules 320"), and a golf assistance application 322. Storage device(s) 314 may also store golf data 324. Golf data 324 may include data regarding golf courses, historical golf play data, data regarding a golfer's average shot distances for a given club, data regarding a golfer's club inventory, and so on.

Execution of instructions associated with operating system 318 may cause mobile device 106 to perform various functions to manage hardware resources of mobile device 106 and to provide various common services for other computer programs. Execution of instructions associated with application modules 320 may cause mobile device 106 to provide various applications (e.g., "apps," operating system applications, etc.). Application modules 320 may provide particular applications, such as text messaging (e.g., SMS) applications, instant messaging applications, email applications, social media applications, text composition applications, web browsers, and so on.

Execution of instructions associated with golf assistance application 322 may cause mobile device 106 to perform various functions described in this disclosure with respect to computing system 104 (FIG. 1). For example, execution of instructions associated with golf assistance application 322 may cause mobile device 106 to configure radio 305 to wirelessly receive data from an ear-wearable device. Additionally, execution of instructions associated with golf assistance application 322 may cause mobile device 106 to determine, based on the data received from the ear-wearable device, a current position of the ear-wearable device. Execution of the instructions associated with golf assistance application 322 may also cause mobile device 106 to determine, based on the current position of the ear-wearable device and data regarding a golf course (e.g., golf data 324), golf advice data that provides a recommendation regarding play of the golf course. Furthermore, execution of the instructions associated with golf assistance application 322 may cause radio 305 to wirelessly send audio data to the ear-wearable device. The audio data may represent soundwaves of a vocalization of the golf advice data. Although not explicitly described here for the sake of brevity, instructions associated with golf assistance application 322 may cause mobile device 106 to perform various other actions of computing system 104.

As shown in the example of FIG. 3, mobile device 106 comprises battery 312 and display screen 308. Display screen 308 may comprise a touch-sensitive screen configured to display information and receive indications of touch input. Thus, in some examples, display screen 308 may be considered one of input device(s) 302 and/or output device(s) 306. Display screen 308 is configured to draw electrical power from battery 312. In accordance with a technique of this disclosure, mobile device 106 is configured such that mobile device 106 refrains from activating display screen 308 throughout the process of providing golf advice data. For instance, execution of the instructions associated with golf assistance application 322 does not cause mobile device 106 to activate display screen 308 when providing the golf advice data. Activating display screen 308 may comprise illuminating a backlight or one or more light-emitting pixel elements of display screen 308, or the like. This may stand in contrast to prior golf assistance applications that are required to activate a display screen, such as a display screen of a mobile device or smartwatch. Refraining from activating a display screen, such as display screen 308, when providing golf advice data may improve mobile device (or a smartwatch or other wearable) by potentially reducing the draw of electrical power from a battery, such as battery 312. Furthermore, not using the display screen to receive user input when providing golf advice data may accelerate user input and increase accuracy of computing system 104 processing the user input. For instance, to use a conventional golf assistance application, a golfer may need to remove his or her gloves prior to using the golf assistance application because touch-sensitive screens frequently do not work when a user is wearing gloves. Additionally, sweat on the golfer's hands may interfere with the touch-sensitive screen and reduce accuracy. Using audio data as described in this disclosure may reduce such problems.

Figure 4:
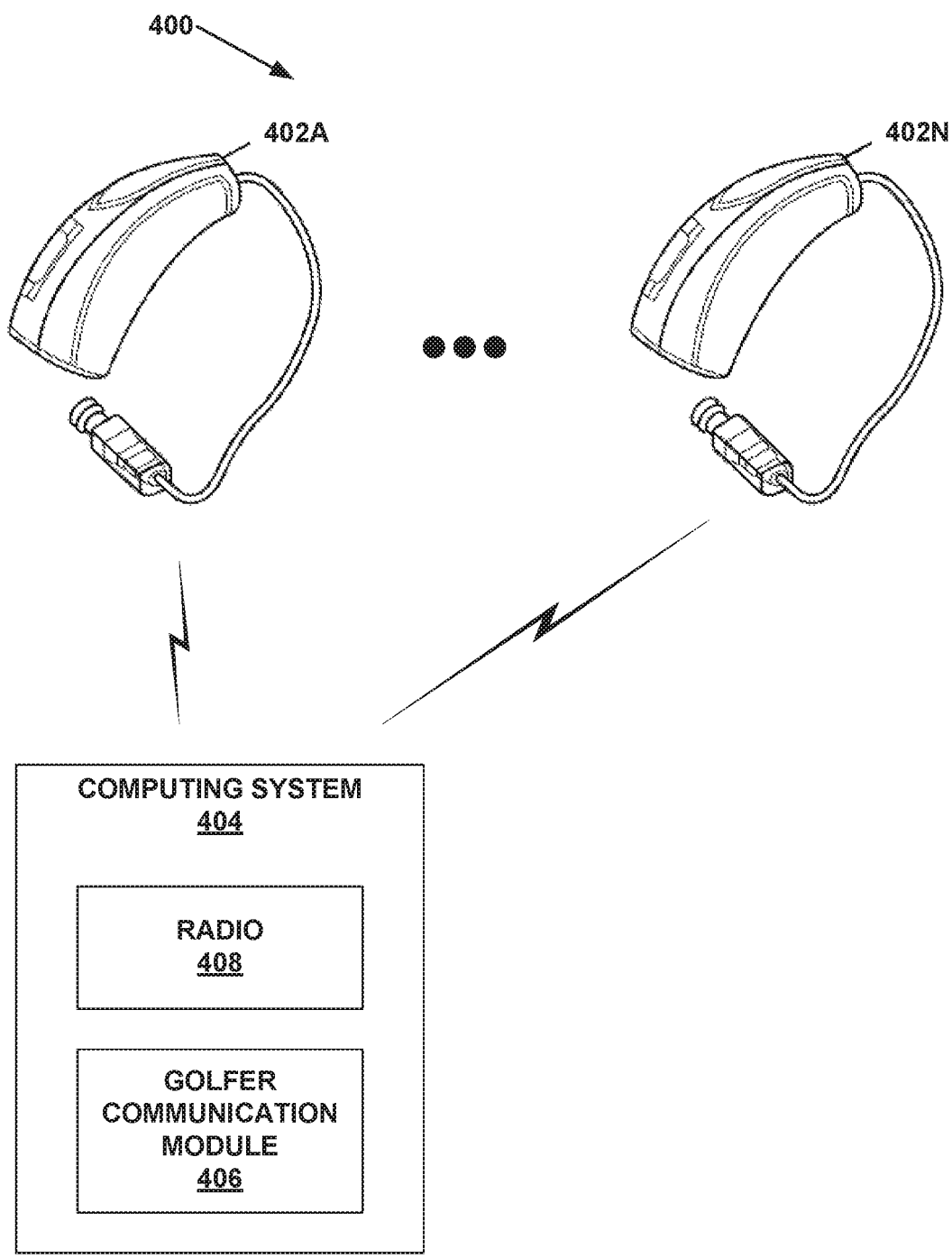
FIG. 4 illustrates an example system in which a computing system facilitates voice communication between people concurrently playing the same hole of a golf course, in accordance with one or more techniques of this disclosure.

FIG. 4 illustrates an example system 400 in which computing system 104 facilitates voice communication between people concurrently playing the same hole of a golf course, in accordance with one or more techniques of this disclosure. Communication between golfers playing on the same hole of a golf course may be important for the golfer's safety and enjoyment. For example, a golfer on a course may need to call "fore" to notify other golfers of a shot being taken. In this example, other golfers may not be able to easily hear the golfer calling fore. In another example, a golfer may wish to tell golfers behind that they can safely shoot. In another example, golfing partners may wish to converse with each other despite being separated on the hole. Techniques of this disclosure may ease communication between people playing the same hole of a golf course.

In the example of FIG. 4, system 400 comprises a plurality of ear-wearable devices 402A through 402N (collectively, "ear-wearable devices 402"). Additionally, system 400 includes a computing system 404. Ear-wearable devices 402 may each be implemented in the same or similar way as ear-wearable device 102 (FIG. 1, FIG. 2) and may perform the functions of ear-wearable device 102 described elsewhere in this disclosure. Furthermore, computing system 404 may be implemented in the same or similar way as computing system 102 (FIG. 1). In the example of FIG. 4, computing system 404 includes a golfer communication module 406. Golfer communication module 406 may be implemented in a mobile device (e.g., mobile device 106 of FIG. 1), a server device (e.g., server device 108 of FIG. 1), or on another type of computing device.

In accordance with one example, golfer communication module 406 receives an indication of user input identifying a playing partner of a wearer of a first ear-wearable device (e.g., ear-wearable device 402A). For example, computing system 404 may comprise a mobile device, such as a smartphone, which displays a user interface on a touch-sensitive screen. In this example, the mobile device may receive the user input via the user interface displayed on the touch-sensitive screen. In another example, computing system 404 may receive audio data representing a vocalization of a name or other identifier of the playing partner. Golfer communication module 406 may determine that a second ear-wearable device (e.g., ear-wearable device 402N) is associated with the playing partner. For instance, golfer communication module 406 may use a directory that maps people to ear-wearable devices to determine that the second ear-wearable device is associated with the playing partner. Subsequently, a radio 408 of computing system 404 may wirelessly receive audio data from the first ear-wearable device. The audio data may represent a vocalization of the wearer of the first ear-wearable device. Responsive to wirelessly receiving the audio data, golfer communication module 406 may cause radio 408 of computing system 404 to wirelessly send, based on the second ear-wearable device being associated with the playing partner, the audio data for receipt by the second ear-wearable device.

Computing system 404 may send the second audio data for receipt by the second ear-wearable device in various ways. For example, computing system 404 may comprise a first mobile device that is communicatively paired with the first ear-wearable device, and a second mobile device that is communicatively paired with the second ear-wearable device, and a server device. In this example, the first mobile device may receive audio data from the first ear-wearable device and forward the audio data to the server device. Golfer communication module 406 may cause the server device, in turn, to forward the audio data to the second mobile device, which forwards the audio data to the second ear-wearable device. When forwarding the audio data to the second mobile device, the server device may send the audio data through a series of devices in a communication network, such as the Internet, a cellular data network, or another type of communication network. In another example, computing system 404 may include a mobile device that communicates wirelessly directly with both the first ear-wearable device and the second ear-wearable device. In this example, the mobile device may receive the audio data from the first ear-wearable device and golfer communication module 406 may cause radio 408 to forward the audio data directly to the second ear-wearable device.

In one example, golfer communication module 406 may automatically determine that a wearer of a second ear-wearable device (e.g., ear-wearable device 402N) is concurrently playing a same hole of the golf course as a wearer of a first ear-wearable device (e.g., ear-wearable device 402A). In this example, radio 408 of computing system 404 may wirelessly receive audio data from the first ear-wearable device. The audio data may represent a vocalization of the wearer of the first ear-wearable device. Furthermore, in this example, responsive to wirelessly receiving the audio data, golfer communication module 406 may cause radio 408 to wirelessly send, based on determining that the wearer of the second ear-wearable device is concurrently playing the same hole of the golf course as the wearer of the first ear-wearable device, the audio data for receipt of the second ear-wearable device. Golfer communication module 406 may automatically determine that the wearer of the second ear-wearable device is concurrently playing the same hole of the golf course as the wearer of the first ear-wearable device in various ways. For example, golfer communication module 406 may determine, based on data received by computing system 404 from the first ear-wearable device, a location associated with the first ear-wearable device. Additionally, golfer communication module 406 may determine, based on data received by computing system 404 from the second ear-wearable device, a location associated with the second ear-wearable device. Golfer communication module 406 may determine the location associated with the first and/or second ear-wearable device in the manner described elsewhere in this disclosure for determining the position of an ear-wearable device. In other instances, golfer communication module 406 may determine the location associated with the first and/or second ear-wearable devices based on GNSS data provided by mobile devices communicatively paired with the first and/or second ear-wearable devices because precise location of the first and/or second ear-wearable devices may be less important in this use case. In this example, golfer communication module 406 may determine, based on the location associated with the second ear-wearable device and the current position of the first ear-wearable device being within a field of play for the same hole of the golf course, that the wearer of the second ear-wearable device is concurrently playing the same hole of the golf course as the wearer of the first ear-wearable device.

Figure 5:
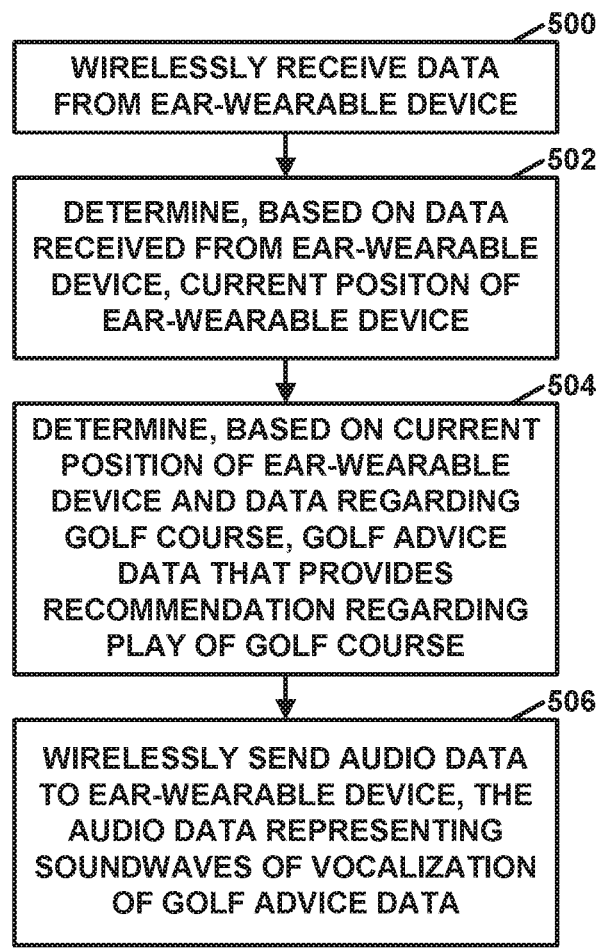
FIG. 5 is a flowchart illustrating an example operation of a computing system, in accordance with one or more aspects of this disclosure.

FIG. 5 is a flowchart illustrating an example operation of computing system 104, in accordance with one or more aspects of this disclosure. The flowcharts of this disclosure are provided as examples. In other examples, operations shown in the flowcharts may include more, fewer, or different actions, or actions may be performed in different orders or in parallel.

In the example of FIG. 5, a radio (e.g., radio 305 of FIG. 3) of computing system 104 may wirelessly receive data from ear-wearable device 102 (500). As previously noted, computing system 104 comprises one or more electronic computing devices, such as mobile device 106, server device 108, and so on.

Furthermore, in the example of FIG. 5, computing system 104 may determine, based on the data received from ear-wearable device 102, a current position of ear-wearable device 102 (502). For instance, computing system 104 may determine current position of ear-wearable device 102 according to the dead-reckoning example provided elsewhere in this disclosure.

Computing system 104 may also determine, based on the current position of ear-wearable device 102 and data regarding a golf course (e.g., golf data 324 of FIG. 3), golf advice data that provides a recommendation regarding play of the golf course (504). Computing system 104 may determine the golf advice data in accordance with any of the examples provided elsewhere in this disclosure. Furthermore, the radio of computing system 104 may wirelessly send audio data to ear-wearable device 102 (506). The audio data may represent soundwaves of a vocalization of the golf advice data.

Figure 6:
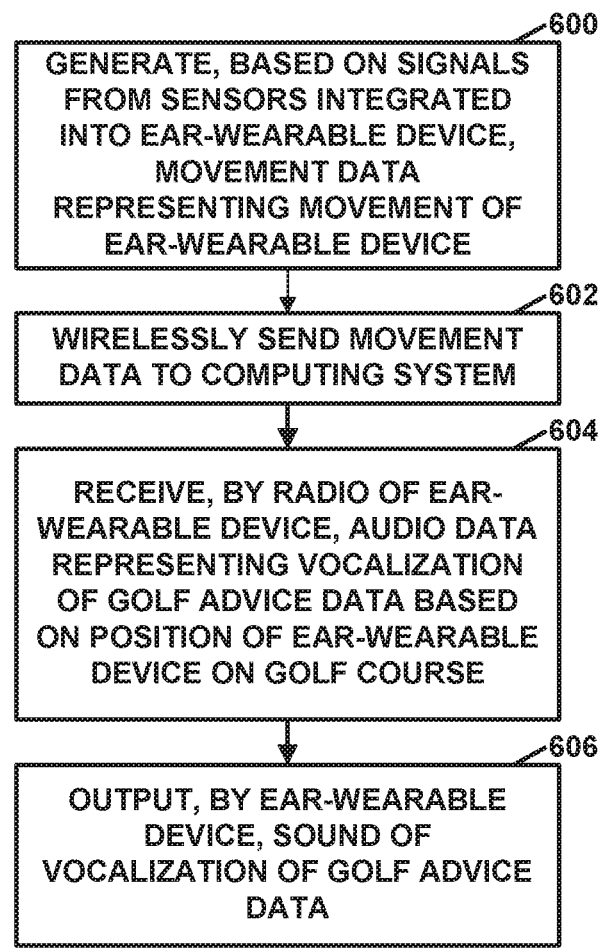
FIG. 6 is a flowchart illustrating an example operation of an ear-wearable device, in accordance with one or more aspects of this disclosure.

FIG. 6 is a flowchart illustrating an example operation of an ear-wearable device, in accordance with one or more techniques of this disclosure. In the example of FIG. 6, ear-wearable device 102 may generate, based on signals from one or more sensors (e.g., sensors 210 (FIG. 2)) integrated into ear-wearable device 102, movement data representing movement of ear-wearable device 102 (600). In some examples, the one or more sensors include one or more accelerometers (e.g., accelerometers 218 (FIG. 2)) and the movement data comprises accelerometer data. Furthermore, a radio (e.g., radio 202 (FIG. 2)) of ear-wearable device 102 may wirelessly send the movement data. to computing system 104 (602). Subsequently, the radio of ear-wearable device 102 may wirelessly receive audio data representing a vocalization of golf advice data based on a position of ear-wearable device 102 on a golf course (604). The golf advice data is determined in part based on the movement data. For instance, computing system 104 may determine the golf advice data in accordance with any of the examples described elsewhere in this disclosure. As in other examples, the golf advice data comprises at least one of: a recommendation of a golf club, a distance of ear-wearable device 102 to a pin, a target position on the golf course at which to aim a next shot, an elevation change between the current position of the ear-wearable device and the target position on the golf course of the next shot, wind conditions at the current position of the ear-wearable device, existence of hazards in the golf course, and so on.

Ear-wearable device 102 may output sound of the vocalization of the golf advice data (606). For instance, receiver 204 (FIG. 2) may generate the sound in response to electrical signals corresponding to the sound.

Although not shown in the example of FIG. 6, ear-wearable device 102 may perform many other activities in addition to or in alternative to the activities shown in FIG. 6. For example, in response to computing system 104 determining based on the current position of ear-wearable device 102 that the wearer of ear-wearable device 102 has completed play of a hole of the golf course, the radio of ear-wearable device 102 may wirelessly receive second audio data. The second audio data may represent soundwaves of a vocalization of a prompt to the wearer of ear-wearable device 102 to provide play result information for the hole. The radio of ear-wearable device 102 may wirelessly send third audio data to computing system 104. The third audio data represents soundwaves of a vocalization of the play result information detected by a microphone of the ear-wearable device.

In another example, ear-wearable device 102 may generate, based on signals generated by sensors integrated into the ear-wearable device, biometric data comprising at least one of heartrate information, body temperature information, galvanic skin response information, or step counts. In this example, the radio of ear-wearable device 102 may wirelessly send the biometric data to computing system 104. Additionally, in this example, the radio of ear-wearable device 102 may wirelessly receive second audio data from computing system 104. In this example, the second audio data is based on the biometric data and represents soundwaves of a vocalization of advice to stop play of the golf course, calm one's self prior to hitting a shot, or drink liquids. Providing advice to stop play of the golf course may be especially valuable for people with heart conditions.

In some examples, biometric data generated by ear-wearable device 102 is used by an activity tracking application. The activity tracking application may run in computing system 104 (e.g., in mobile device 106). The activity tracking application may record user activity and provide feedback to a user regarding the user's level of physical activity. Activity tracking applications have become popular as a way of encouraging people to be more active and less sedentary.

Figure 7:
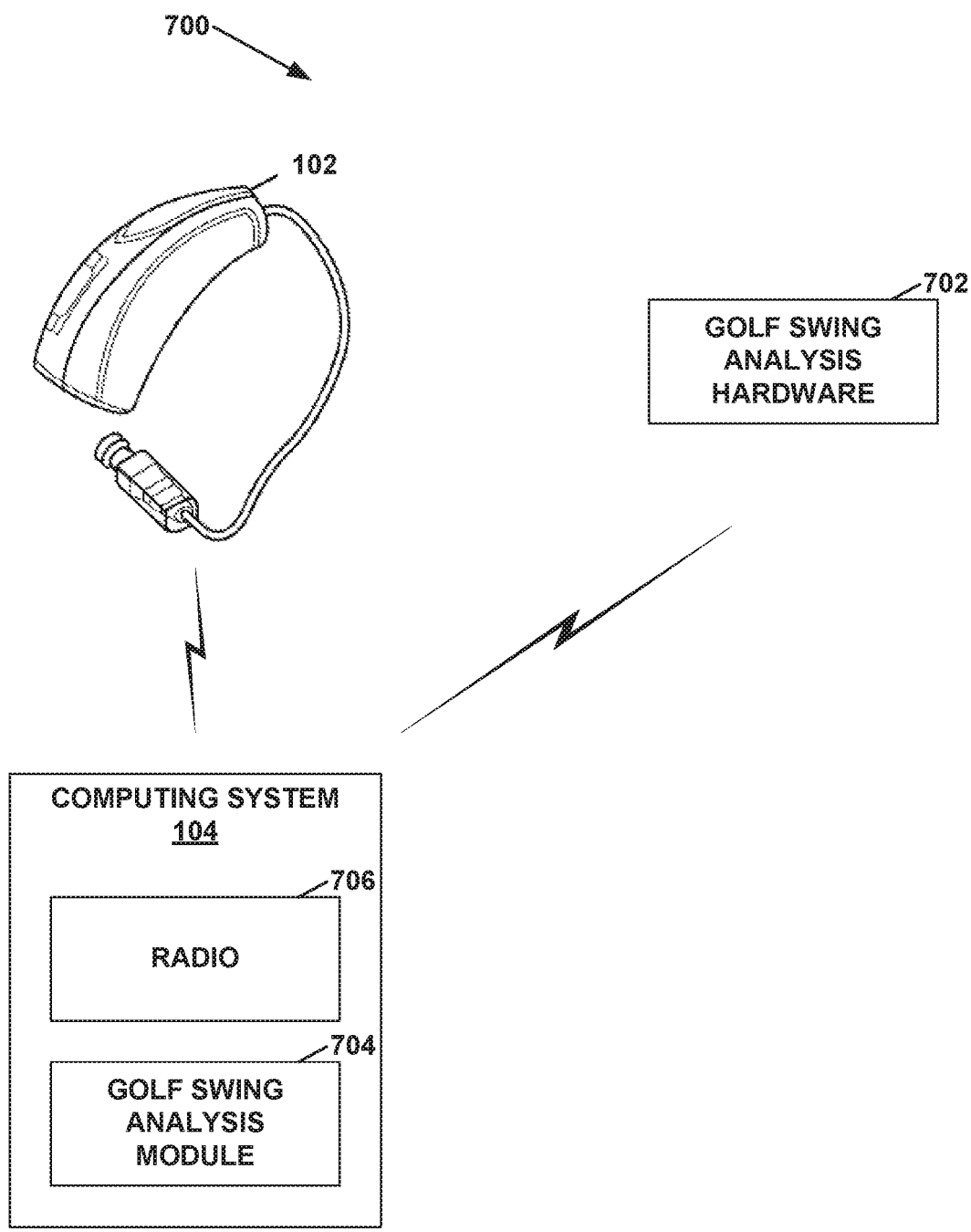
FIG. 7 is a block diagram illustrating an example system for providing golf advice data that includes swing analysis hardware, in accordance with one or more aspects of this disclosure.

FIG. 7 is a block diagram illustrating an example system 700 for providing golf advice data that includes swing analysis hardware 702, in accordance with one or more aspects of this disclosure. Swing analysis hardware 702 may comprise several types of devices. For example, swing analysis hardware 702 may comprise a device that attaches to a club, a device included in or attached to a golfer's glove or wristband, a device that uses cameras to watch a golfer's swing, and so on. In the example of FIG. 7, computing system 104 comprises a golf swing analysis module 704. Golf swing analysis module 704 may be implemented in mobile device 106 (FIG. 1), server device 108 (FIG. 1), or in another component of computing system 104. A radio 706 of computing system 104 may receive data from golf swing analysis hardware 702. Golf swing analysis module 704 may use data from accelerometers in ear-wearable device 102 and the data from golf swing analysis hardware 702 to analyze a golfer's swing. For example, the data from an accelerometer in an ear-worn device can provide information about head movement (up/down, side-side sway) while the hardware attached to a club will provide swing plane and acceleration data. Combining these different data sources can lead to faster learning about overall swing mechanics. Data in isolation that from hardware attached to a club is only one component and a golfer may be executing a good swing plane but the golfer may be out of position for a solid ball strike due to head movements.

In some examples, golf swing analysis module 704 may use data from one or more accelerometers in ear-wearable device 102 to identify and calculate, or recall, body position of a golfer when addressing the ball, and throughout the entire swing. There are many components that can impact the golfer body position such as grip on the club, hand position, spine tilt, posture, foot placement and knee bend. In this example, golf swing analysis module 704 may calibrate a body position from accelerometer data when ear-worn device 102 is initially worn, and body position measurements by the accelerometers measured with respect of the calibrated body position. Body position calibration could be the result of a professional consultation, and the user can be alerted via accelerometer data and processing to being out of the desired body position at setup and during the swing. In another example, the accelerometer senses motion related to swing flaws such as reverse pivot, lunging, dipping, standing up, weight transfer faults, too much arm swing, rotational faults, follow through faults, swing finish faults, swing synchronization faults. Golf swing analysis module 704 may store data generated by the one or more accelerometers and may analysis the data to identify faults in a golfer's swing mechanics and body positioning.

Additionally, golf swing analysis module 704 may cause radio 706 to send audio data to ear-wearable device 102. Golf swing analysis module 704 may generate the audio data by analyzing the stored data. In some examples, golf swing analysis module 704 uses an artificial neural network algorithm trained using accelerometer data tagged with data indicating swing faults to identify swing faults in the swing of a wearer of ear-wearable device 102. The audio data may indicate a recommendation on how to improve the swing of the wearer of ear-wearable device 102. In some examples, golf swing analysis module 704 or another application may output one or more user interfaces for display containing advice based on the stored data.

Figure 8:
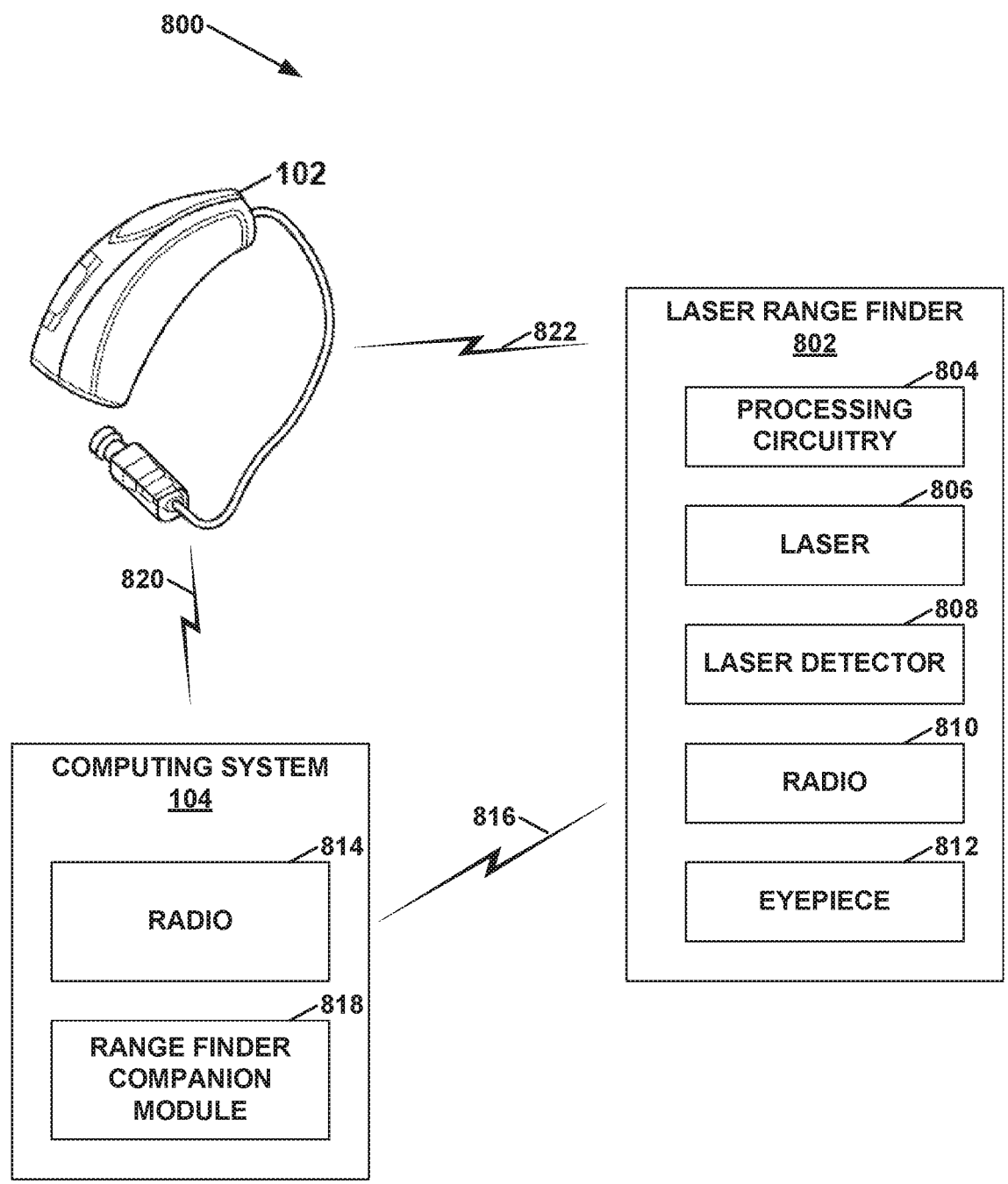
FIG. 8 is a block diagram illustrating an example system for providing golf advice data that includes a range finder, in accordance with one or more aspects of this disclosure.

FIG. 8 is a block diagram illustrating an example system 800 for providing golf advice data that includes a laser range finder 802, in accordance with one or more aspects of this disclosure. In the example of FIG. 8, laser range finder 802 comprises processing circuitry 804, a laser 806, a laser detector 808, a radio 810, and an eyepiece 812. Laser 806 is configured to emit a laser beam. Laser detector 808 is configured to detect a reflection of the laser beam. Processing circuitry 804 of laser range finder 802 determines a distance based on a time of flight of the laser beam emitted by laser 806. A golfer uses laser range finder 802 to determine a distance to a target location, such as a green or mid-hole location. To use laser range finder 802, the golfer raises eyepiece 812 of laser range finder 802 to the golfer's eye and looks at the target location. Conventionally, laser range finders display text indicating the distance to the target location in the eyepiece or on a separate display of the laser range finder. However, conveying the distance in text form may make it challenging for people, especially more senior golfers, who struggle with reading small text to use laser range finders.

Techniques of this disclosure may overcome this challenge in laser range finders. In accordance with a technique of this disclosure, ear-wearable device 102 outputs an audible vocalization of range data generated by laser range finder 802. For instance, if laser range finder 802 determines that the distance to a target location is 100 yards, ear-wearable device 102 may generate sound of a voice saying "100 yards."

In one example, processing circuitry 804 of laser range finder 802 causes radio 810 to communicate range data to a radio 814 of computing system 104 via a communication link 816. In some examples, radio 814 is included in a mobile device, such as mobile device 106 (FIG. 1). In this example, a range finder companion module 818 may process the range data to generate audio data representing soundwaves of a vocalization of the range. Range finder companion module 818 may then cause radio 806 to wirelessly send the audio data to ear-wearable device 102 via a communication link 820. Based on the audio data, ear-wearable device 102 outputs the soundwaves of the vocalization of the range. Thus, in this example, computing system 104 may wirelessly receive, from laser range finder 802, data indicating a distance from laser range finder 802 to a target location and computing system 104 may wirelessly send audio data to ear-wearable device 102, where the audio data representing soundwaves of a vocalization of the distance.

Communication link 816 and communication link 820 may be Bluetooth communication channels, or any of the other types of wireless communication channels discussed elsewhere in this disclosure. In some examples, range finder companion module 818 comprises instructions that, when executed by processors in computing system 104, cause the processors to perform the actions ascribed in this disclosure to range finder companion module 818.

In another example, processing circuitry 804 of laser range finder 802 causes radio 810 to communicate audio data representing soundwaves of a vocalization of range data directly to ear-wearable device 102 via a communication link 822. Thus, in this example, based on the audio data, ear-wearable device 102 outputs the soundwaves of the vocalization of the range data. Communication link 822 may be a Bluetooth communication channel, or any of the other types of wireless communication channels discussed elsewhere in this disclosure.

Thus, in the example of FIG. 8, laser range finder 802 comprises a radio, a laser configured to emit a laser beam, a laser detector configured to detect a reflection of the laser beam, and processing circuitry. The processing circuitry is configured to determine, based on the reflection of the laser beam, a distance to a target location. Additionally, the processing circuitry is configured to cause the radio to wirelessly send, to a remote device, data indicating the distance. In this example, the data indicating the distance may comprise audio data representing soundwaves of a vocalization of the distance. Furthermore, in some instances, the remote device of this example is ear-wearable device 102. In other instances, the remote device is a computing system (e.g., computing system 104 configured to send the audio data to ear-wearable device 102.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and disc, where disks usually reproduce data magnetically, while discs reproduce data optically with lasers. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A method comprising:
    wirelessly receiving, by a computing system, first data from an ear-wearable device, the computing system comprising one or more electronic computing devices;
    determining, by the computing system, based on the first data received from the ear-wearable device, a current position of the ear-wearable device;
    determining, by the computing system, based on the current position of the ear-wearable device and data regarding a golf course, first golf advice data that provides a recommendation regarding play of the golf course;

wirelessly sending, by the computing system, first audio data to the ear-wearable device, the first audio data representing soundwaves of a vocalization of the first golf advice data;

wirelessly receiving, by the computing system, second audio data from the ear-wearable device, the second audio data representing incoming soundwaves detected by the ear-wearable device;

determining, by the computing system, based on the second audio data and based on the data regarding the golf course, second golf advice data that provides a second recommendation regarding play of the golf course; and wirelessly sending, by the computing system, third audio data to the ear-wearable device, the third audio data representing soundwaves of a vocalization of the second golf advice data.

2. The method of claim 1, wherein:
the method further comprises determining, by the computing system, based on Global Navigation Satellite System (GNSS) data, an initial location of the ear-wearable device at a time when a signal strength of a radio signal generated by an ear-wearable device as detected by a radio of the computing system is above a threshold, the first data received from the ear-wearable device comprises data indicative of movements of the ear-wearable device, and wherein determining the current position of the ear-wearable device comprises calculating, via dead reckoning using the initial location of the ear-wearable device and the data indicative of the movements of the ear-wearable device, the current position of the ear-wearable device.

3. The method of claim 2, wherein the data indicative of the movements of the ear-wearable device comprise accelerometer data.

4. The method of claim 1, wherein determining the golf advice data comprises determining, by the computing system, based on where the current position of the ear-wearable device is on the golf course, at least one of: a recommendation of a golf club, a distance of the ear-wearable device to a hole, a target position on the golf course at which to aim a next shot, an elevation change between the current position of the ear-wearable device and the target position on the golf course of the next shot, wind conditions at the current position of the ear-wearable device, or existence of hazards in the golf course.

5. The method of claim 1, wherein determining the current position of the ear-wearable device comprises determining, by the computing system, based on GNSS data included in the first data received from the ear-wearable device, the current position of the ear-wearable device.

6. The method of claim 1, wherein the one or more electronic computing devices in the computing system include a mobile device.

7. The method of claim 1, wherein:
the incoming soundwaves represent a vocalization of a question regarding the golf course or environmental conditions at the golf course; and determining the second golf advice data comprises: determining, by the computing system, based on the second audio data and based on the data regarding the golf course, the second golf advice data such that the second golf advice data comprises an answer to the question.

8. The method of claim 1, wherein:
the first data received from the ear-wearable device comprises data indicative of movements of the ear-wearable device, and the method further comprises:
determining, by the computing system, based on the data indicative of the movements of the ear-wearable device, second golf advice data, wherein the second golf advice data provides a recommendation on improving a golf swing; and wirelessly sending, by the computing system, fourth audio data to the ear-wearable device, the fourth audio data representing soundwaves of a vocalization of the second golf advice data.

9. The method of claim 1, wherein the method further comprising:
determining, by the computing system, based on the current position of the ear-wearable device, that a wearer of the ear-wearable device has completed play of a hole of the golf course;

in response to determining that the wearer of the ear-wearable device has completed play of the hole, wirelessly sending, by the computing system, fourth audio data to the ear-wearable device, the fourth audio data representing soundwaves of a vocalization of a prompt to the wearer of the ear-wearable device to provide play result information for the hole;

wirelessly receiving, by the computing system, fifth audio data from the ear-wearable device, the fifth audio data representing soundwaves of a vocalization of the play result information; and responsive to wirelessly receiving the fifth audio data, storing, by the computing system, the play result information for subsequent retrieval, wherein the play result information comprises at least one of: a score for the hole, a number of putts, fairway hits and misses, sand shots, or penalty shots.

10. The method of claim 1, wherein:
the method further comprises:
wirelessly receiving, by the computing system, biometric data from the ear-wearable device, the biometric data comprising at least one of heartrate information, body temperature information, or a number of steps taken;

determining, by the computing system, based on the biometric data, whether a wearer of the ear-wearable device should stop play of the golf course; and responsive to determining the wearer of the ear-wearable device should stop play of the golf course, wirelessly sending, by the computing system, fourth audio data to the ear-wearable device, the fourth audio data representing soundwaves of a vocalization of advice to stop play of the golf course.

11. The method of claim 1, wherein the ear-wearable device is a first ear-wearable device, the method further comprising:
receiving, by the computing system, an indication of user input identifying a playing partner of a wearer of the ear-wearable device;

determining, by the computing system, that a second ear-wearable device is associated with the playing partner;

wirelessly receiving, by the computing system, fourth audio data from the first ear-wearable device, the fourth audio data representing a vocalization of the wearer of the first ear-wearable device; and responsive to wirelessly receiving the fourth audio data, wirelessly sending, by the computing system, based on the second ear-wearable device being associated with the playing partner, the fourth audio data for receipt by the second ear-wearable device.

12. The method of claim 1, wherein the ear-wearable device is a first ear-wearable device, the method further comprising:
   automatically determining, by the computing system, that a wearer of a second ear-wearable device is concurrently playing a same hole of the golf course as a wearer of the first ear-wearable device;
   wirelessly receiving, by the computing system, fourth audio data from the first ear-wearable device, the fourth audio data representing a vocalization of the wearer of the first ear-wearable device; and
   responsive to wirelessly receiving the fourth audio data, wirelessly sending, by the computing system, based on determining that the wearer of the second ear-wearable device is concurrently playing the same hole of the golf course as the wearer of the first ear-wearable device, the fourth audio data for receipt of the second ear-wearable device.

13. A computing system comprising:
   a radio; and
   one or more electronic computing devices configured to:
      configure the radio to wirelessly receive first data from an ear-wearable device;
      determine, based on the first data received from the ear-wearable device, a current position of the ear-wearable device;
      determine, based on the current position of the ear-wearable device and data regarding a golf course, first golf advice data that provides a recommendation regarding play of the golf course;
      cause the radio to wirelessly send first audio data to the ear-wearable device, the first audio data representing soundwaves of a vocalization of the first golf advice data;
      wirelessly receive second audio data from the ear-wearable device, the second audio data representing incoming soundwaves detected by the ear-wearable device;
      determine, based on the second audio data and based on the data regarding the golf course, second golf advice data that provides a second recommendation regarding play of the golf course; and
      wirelessly send third audio data to the ear-wearable device, the third audio data representing soundwaves of a vocalization of the second golf advice data.

14. The computing system of claim 13, wherein the one or more electronic devices are further configured to determine, based on Global Navigation Satellite System (GNSS) data, an initial location of the ear-wearable device at a time when a signal strength of a radio signal generated by an ear-wearable device as detected by the radio of the computing system is above a threshold; and
   the first data received from the ear-wearable device comprises data indicative of movements of the ear-wearable device, and
   wherein determining the current position of the ear-wearable device comprises calculating, via dead reckoning using the initial location of the ear-wearable device and the data indicative of the movements of the ear-wearable device, the current position of the ear-wearable device.

15. The computing system of claim 14, wherein the data indicative of the movements of the ear-wearable device comprise at least one of accelerometer data and orientation data.

16. A non-transitory computer-readable storage medium having instructions stored thereon that, when executed, cause a computing system comprising one or more electronic computing devices to:
   configure a radio of the computing system to wirelessly receive first data from an ear-wearable device;
   determine, based on the first data received from the ear-wearable device, a current position of the ear-wearable device;
   determine, based on the current position of the ear-wearable device and data regarding a golf course, first golf advice data that provides a recommendation regarding play of the golf course;
   cause the radio to wirelessly send first audio data to the ear-wearable device, the first audio data representing soundwaves of a vocalization of the first golf advice data;
   wirelessly receive second audio data from the ear-wearable device, the second audio data representing incoming soundwaves detected by the ear-wearable device;
   determine, based on the second audio data and based on the data regarding the golf course, second golf advice data that provides a second recommendation regarding play of the golf course; and
   wirelessly send third audio data to the ear-wearable device, the third audio data representing soundwaves of a vocalization of the second golf advice data.

17. The non-transitory computer-readable storage medium of claim 16, wherein execution of the instructions further causes the computing system to determine, based on Global Navigation Satellite System (GNSS) data, an initial location of the ear-wearable device at a time when a signal strength of a radio signal generated by an ear-wearable device as detected by the radio of the computing system is above a threshold,
   the first data received from the ear-wearable device comprises data indicative of movements of the ear-wearable device, and
   wherein the instructions cause the computing system to calculate, via dead reckoning using the initial location of the ear-wearable device and the data indicative of the movements of the ear-wearable device, the current position of the ear-wearable device.

18. The non-transitory computer-readable storage medium of claim 17, wherein the data indicative of the movements of the ear-wearable device comprise at least one of accelerometer data and orientation data.

19. The non-transitory computer-readable storage medium of claim 16, wherein determining the golf advice data comprises determining, by the computing system, based on where the current position of the ear-wearable device is on the golf course, at least one of: a recommendation of a golf club, a distance of the ear-wearable device to a hole, a target position on the golf course at which to aim a next shot, an elevation change between the current position of the ear-wearable device and the target position on the golf course of the next shot, wind conditions at the current position of the ear-wearable device, or existence of hazards in the golf course.

20. The non-transitory computer-readable storage medium of claim 16, wherein:
the incoming soundwaves represent a vocalization of a question regarding the golf course or environmental conditions at the golf course, and
execution of the instructions causes the computing system to determine, based on the second audio data and based on the data regarding the golf course, the second golf advice data such that the second golf advice data comprises an answer to the question.

21. The non-transitory computer-readable storage medium of claim 16, wherein:
the first data received from the ear-wearable device comprises data indicative of movements of the ear-wearable device,
the golf advice data is first golf advice data and execution of the instructions further causes the computing system to:
determine, based on the data indicative of the movements of the ear-wearable device, second golf advice data, wherein the second golf advice data provides a recommendation on improving a golf swing; and
wirelessly send fourth audio data to the ear-wearable device, the fourth audio data representing soundwaves of a vocalization of the second golf advice data.

22. The non-transitory computer-readable storage medium of claim 16, wherein execution of the instructions further causes the computing system to:
determine, based on the current position of the ear-wearable device, that a wearer of the ear-wearable device has completed play of a hole of the golf course;
in response to determining that the wearer of the ear-wearable device has completed play of the hole, wirelessly send fourth audio data to the ear-wearable device, the fourth audio data representing soundwaves of a vocalization of a prompt to the wearer of the ear-wearable device to provide play result information for the hole;
wirelessly receive fifth audio data from the ear-wearable device, the fifth audio data representing soundwaves of a vocalization of the play result information; and
responsive to wirelessly receiving the fifth audio data, store the play result information for subsequent retrieval,
wherein the play result information comprises at least one of: a score for the hole, a number of putts, fairway hits and misses, sand shots, or penalty shots.

23. The non-transitory computer-readable storage medium of claim 16, wherein and execution of the instructions further causes the computing system to:
wirelessly receive biometric data from the ear-wearable device, the biometric data comprising at least one of heartrate information, body temperature information, or a number of steps taken;
determine, based on the biometric data, whether a wearer of the ear-wearable device should stop play of the golf course; and
responsive to determining the wearer of the ear-wearable device should stop play of the golf course, wirelessly send fourth audio data to the ear-wearable device, the fourth audio data representing soundwaves of a vocalization of advice to stop play of the golf course.

24. The non-transitory computer-readable storage medium of claim 16, wherein the ear-wearable device is a first ear-wearable device and execution of the instructions further causes the computing system to:
receive an indication of user input identifying a playing partner of a wearer of the ear-wearable device;
determine that a second ear-wearable device is associated with the playing partner;
wirelessly receive fourth audio data from the first ear-wearable device, the fourth audio data representing a vocalization of the wearer of the first ear-wearable device; and
responsive to wirelessly receiving the fourth audio data, wirelessly send, based on the second ear-wearable device being associated with the playing partner, the fourth audio data for receipt by the second ear-wearable device.

25. The non-transitory computer-readable storage medium of claim 16, wherein the ear-wearable device is a first ear-wearable device and execution of the instructions further causing the computing system to:
automatically determine that a wearer of a second ear-wearable device is concurrently playing a same hole of the golf course as a wearer of the first ear-wearable device;
wirelessly receive fourth audio data from the first ear-wearable device, the fourth audio data representing a vocalization of the wearer of the first ear-wearable device; and
responsive to wirelessly receiving the fourth audio data, wirelessly send, based on determining that the wearer of the second ear-wearable device is concurrently playing the same hole of the golf course as the wearer of the first ear-wearable device, the fourth audio data for receipt of the second ear-wearable device.

26. An ear-wearable device comprising:
a radio;
one or more accelerometers;
a receiver; and
one or more processors configured to:
generate, based on signals from the one or more accelerometers, movement data representing movement of the ear-wearable device;
cause the radio to wirelessly send the movement data to a computing system;
configure the radio to wirelessly receive, from the computing system, a request that a wearer of the ear-wearable device provide a score for a hole of the golf course based on the computing system having determined based on the movement data that the wearer of the ear-wearable device has completed the hole; and
cause the receiver to output sound of a vocalization of a prompt to the wearer of the ear-wearable device to provide the score for the hole.

27. The ear-wearable device of claim 26, wherein the one or more processors are further configured to:
in response to the computing system determining based on a current position of the ear-wearable device that the wearer of the ear-wearable device has completed play of the hole of the golf course, configure the radio to wirelessly receive audio data, the audio data representing soundwaves of a vocalization of a prompt to the wearer of the ear-wearable device to provide play result information for the hole, the play result information including the score for the hole; and
cause the radio to wirelessly send third audio data to the computing system, the third audio data representing soundwaves of a vocalization of the play result information detected by a microphone of the ear-wearable device.

28. The ear-wearable device of claim 26, wherein the ear-wearable device includes one or more sensors integrated into the ear-wearable device, and the one or more processors are further configured to:
generate, based on signals generated by the one or more sensors, biometric data comprising at least one of heartrate information or body temperature information;
cause the radio to wirelessly send the biometric data to the computing system; and
configure the radio to wirelessly receive audio data from the computing system, the audio data being based on the biometric data, the audio data representing soundwaves of a vocalization of advice to stop play of the golf course.

29. A method comprising:
automatically determining, by a computing system, that a wearer of a first ear-wearable device is concurrently playing a same hole of a golf course as a wearer of a second ear-wearable device;
wirelessly receiving, by the computing system, audio data from the first ear-wearable device, the audio data representing a vocalization of the wearer of the first ear-wearable device; and
responsive to wirelessly receiving the audio data, wirelessly sending, by the computing system, based on determining that the wearer of the first ear-wearable device is concurrently playing the same hole of the golf course as the wearer of the second ear-wearable device, the audio data for receipt of the second ear-wearable device.

30. A method comprising:
generating, by one or more processors of an ear-wearable device, based on signals from one or more accelerometers of the ear-wearable device, movement data representing movement of the ear-wearable device;
causing, by the one or more processors of the ear-wearable device, a radio of the ear-wearable device to wirelessly send the movement data to a computing system;
configuring, by the one or more processors of the ear-wearable device, the radio to wirelessly receive, from the computing system, a request that a wearer of the ear-wearable device provide a score for a hole of the golf course based on the computing system having determined based on the movement data that the wearer of the ear-wearable device has completed the hole; and
causing, by the one or more processors of the ear-wearable device, a receiver of the ear-wearable device to output sound of a vocalization of a prompt to the wearer of the ear-wearable device to provide the score for the hole.

* * * * *